United States Patent [19]
Bourinbaiar

[11] Patent Number: 5,837,729
[45] Date of Patent: Nov. 17, 1998

[54] METHODS FOR TREATING AND PREVENTING HIV INFECTION USING ACETAMINOPHEN AND DERIVATIVES THEREOF

[75] Inventor: Aldar S. Bourinbaiar, New York, N.Y.

[73] Assignee: Metatron, Inc., Deer Park, N.Y.

[21] Appl. No.: 638,098

[22] Filed: Apr. 26, 1996

[51] Int. Cl.$^6$ .................................................. A61K 31/24
[52] U.S. Cl. .......................... 514/535; 514/629; 514/934
[58] Field of Search ..................................... 514/534, 624, 514/934

[56] References Cited

U.S. PATENT DOCUMENTS

| | | | |
|---|---|---|---|
| 2,998,450 | 8/1961 | Willbert et al. | 514/629 |
| 4,423,069 | 12/1983 | Kaminski et al. | 514/629 |

FOREIGN PATENT DOCUMENTS 453577  12/1927  Germany .

OTHER PUBLICATIONS

Burger et al, JAMA Abstracts, Ann Pharmacother, vol. 28, pp. 327–330, Mar. 1994.

Lebovits et al, JAMA Abstracts, Clin. J. Pain, vol. 10. pp. 156–161, Jun. 1994.

Bourinbaiar & Fruhstorfer, AIDS 10:558, 1996.

Bourinbaiar & Lee–Huang, Contraception 51:319, 1995.

Bourinbaiar & Lee–Huang, Adv. Exp. Med. Biol. 374:71, 1995.

Bourinbaiar & Lee–Huang, FEBS Lett. 360:85, 1995.

Bourinbaiar & Lee–Huang, Biochem. Biophys. Res. Comm. 208:779, 1995.

Fairbrother in "Analytical Profiles . . . " ed. K. Florey, Academic Press, NY, NY, 1975, pp. 1–109.

Kamindki et al., Contraception 32:183, 1985.

Steffe et al., J. Acquir. Immune Def. Syndr. 3:691, 1990.

Zimmerman, Arch. Intern Med. 141:333, 1981.

*Primary Examiner*—James H. Reamer
*Attorney, Agent, or Firm*—Henry D. Coleman; R. Neil Sudol

[57] ABSTRACT

The present invention relates to the use of acetaminophen (Tylenol) and derivatives thereof which can be used to inhibit the growth, replication and elaboration of the human immunodeficiency virus (HIV). The present invention comprises in vitro as well as in vivo methods for the prevention and/or treatment of HIV infections and acquired immune deficiency syndrome (AIDS), at doses of acetaminophen or its derivatives which are effective to inhibit the replication, growth and/or elaboration of HIV.

15 Claims, 3 Drawing Sheets

METHODS FOR TREATING AND PREVENTING HIV INFECTION USING ACETAMINOPHEN AND DERIVATIVES THEREOF

FIELD OF THE INVENTION

The present invention is directed to methods of preventing and treating HIV infections using acetaminophen and pharmaceutically acceptable derivatives thereof. The present invention relates to the discovery that acetaminophen and a number of pharmaceutically acceptable derivatives, thereof may be used to inhibit the growth, replication and elaboration of HIV in humans. This invention is useful for treating and/or preventing retroviral infections such as HIV infections and the underlying immunodeficiency state known as AIDS.

BACKGROUND OF THE INVENTION

Human immunodeficiency viruses (HIV) of type 1 and 2 belong to the family of retroviruses and are considered to cause acquired immunodeficiency syndrome (AIDS). Human T lymphotropic viruses (HTLV) of type 1 and 2 are also human retroviruses and cause adult T cell leukemia and neurodegenerative diseases. Thus, there are several types of pathogenic retroviruses which can be harmful to humans. The transmission of HIV through sexual contact accounts for up to 90% of AIDS cases worldwide. This transmission is initiated by the passage of HIV across the mucosal barrier of the vagina, penis or rectum when exposed to infectious genital fluids such as semen or vaginal secretions. Increased public awareness of the sexual modes of HIV transmission has been of little consequence in reducing or curbing the AIDS epidemic. Although research activity in the area of finding effective anti-HIV agents has increased in recent years, effective compounds with anti-HIV activity that could be used to prevent transmission and/or treat HIV infections are still lacking. For example, early results with certain spermicidal agents, e.g., the nonionic surfactant, nonoxynol-9, appeared to be quite promising, but it has become clear that local toxicity of this agent is incompatible with its antiviral activity when used at an effective concentration. This shortcoming is due to the fact that the selective index (i.e., the ratio of cytotoxicity to antiviral activity as a function of drug concentration) of nonoxynol-9 (Bourinbaiar & Fruhstorfer *AIDS*, 10:14, 1996). Similar toxicity concerns have arisen with the broad use of azidothymidine (AZT).

A number of nucleoside and non-nucleoside compounds which exhibit activity against retroviral reverse transcriptase, have been posited for the treatment of AIDS, but are not without their limitations. In addition, recently introduced new drugs, such as HIV protease inhibitors, are difficult to manufacture and have shown low oral availability which requires frequent intake of large doses. Consequently, the present methods of preventing and treating HIV are limited and better alternative compounds with higher availability and selectivity must be sought.

The present inventor has discovered several classes of pharmaceutical compounds that were able to inhibit HIV replication without producing significant cytotoxicity in the host patient. Among these agents are cimetidine, mostly known as an anti-ulcer agent, and gramicidin, known as a topical antibiotic and contraceptive agent. The present inventor has also established an anti-HIV effect and the potential for AIDS therapy of several other drugs—previously used for clinical conditions unrelated to HIV infections. Among these agents are warfarin (oral HIV protease inhibitor), coumarins, bestatin, human chorionic gonadotropin, levamisole, estrogen, progesterone, and steroid anti-inflammatory agents such as dexamethasone (see the review Bourinbaiar & Lee-Huang, *Adv. Exp. Med. Biol.* 374:71–89, 1995). Some but not all non-steroidal anti-inflammatory drugs (NSAIDs) have also been shown to be effective against HIV (Bourinbaiar & Lee-Huang, *FEBS Letters,* 360:85–88, 1995). Although indomethacin was shown to be more potent than aspirin, NSAIDs in general are quite toxic, ruling out the possibility that these drugs alone could be used as effective therapies against HIV (Bourinbaiar & Lee-Huang, *Biochem. Biophys. Res. Comm.* 208:779–785, 1995).

Today's world is characterized by both the exponential growth of the human population and an uncurbed epidemic of sexually transmitted AIDS. The discovery of effective anti-AIDS compounds and the development of contraceptive devices that can display anti-HIV activity in topical formulations are priority issues. In the past few years, the present inventor has spent considerable time researching compounds that might be useful in the prevention of sexual transmission of HIV and for the treatment of HIV infection. As a result, several potentially useful antiviral compounds were identified, including gramicidin, cimetidine, warfarin, coumarins, bestatin, human chorionic gonadotropin, levamisole, dexamethasone and select NSAIDs such as indomethacin, among others. It is clear, however, that the efforts in preventing the spread of HIV infections through sexual intercourse and treating AIDS will depend on the larger choice of diverse types of pharmaceutical agents with antiviral potential that could be used either alone or in combination with other active agents.

Acetaminophen, also known by brand names such as Tylenol, APAP, Panadol, Paracetamol, etc., is an over-the-counter analgesic used worldwide for more than four decades. Acetaminophen has a reputation as a generally safe and effective drug. Clinically, acetaminophen is given in a single dose of up to 1,000 mg, once a day or several times a day, with a maximum daily dose of 4,000 mg. Sensitivity reactions may occur occasionally. Overdose or consumption of acetaminophen with alcohol can cause hepatotoxicity which can be reversed by giving N-acetylcysteine to restore glutathione availability (Zimmerman, H. J., *Arch. Intern. Med.* 141:333–342, 1981).

Acetaminophen does not belong to the NSAIDs category since it has no anti-inflammatory activity. While this drug has been studied extensively as an analgesic, it was not obvious that it may have anti-HIV activity. The present inventor was the first to discover that acetaminophen and its derivatives display anti-HIV activity at non-toxic doses.

Acetaminophen was first synthesized in 1878 by reducing p-nitrophenol with tin in glacial acetic acid. Metabolic reduction of oral acetaminophen or acetaminophen prodrug forms given intravenously may result in formation of sulfate, phosphate and glucuronide active metabolites, among others, as well as other metabolites with toxic potential such as acetimidoquinone.

Acetaminophen may be represented by the following chemical formula:

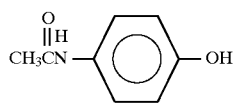

Substituted acetaminophen compounds are known in the art as disclosed, for example, in U.S. Pat. No. 4,423,069, which is incorporated by reference.

OBJECTS OF THE INVENTION

Accordingly, it is an object of the present invention is to provide a method for suppressing HIV infection in vitro.

It is another object of the present invention to provide a method to inhibit or prevent the growth, replication or elaboration of HIV in vivo.

It is still a further object of the present invention to provide a method to prevent the transmission of HIV in vitro.

It is also an object of the present invention to provide a method to prevent the transmission of HIV during sexual intercourse.

It is still a further object of the present invention to provide a method to prevent or treat HIV infections in humans using the present compounds alone or in combination with other pharmaceutical agents having anti-HIV activity.

These and/or other objects of the present invention may be readily gleaned from the description of the present invention which follows.

SUMMARY OF THE INVENTION

The present invention relates to a method for preventing or inhibiting HIV growth, replication and/or elaboration and spread in vitro as well as in vivo using acetaminophen and derivatives thereof alone or in combination with other pharmaceutical agents exhibiting anti-HIV activity.

More specifically, the present invention comprises a method for suppressing HIV growth, replication and/or elaboration and spread by employing anti-HIV effective doses or concentrations of acetaminophen or derivatives, thereof. In the present invention, an HIV effective concentration or dose of acetaminophen or a derivative, thereof is used to inhibit the growth elaboration and/or replication of HIV in an in vitro setting, in an in vivo setting, or in settings to treat organs and body fluids including, for example, prior to transplant procedures and transfusions or before the administration of blood components. In in vitro settings, the present compounds may be used in comparative tests to determine the potential anti-HIV activity of newly discovered agents and in diagnostic tests. In preferred methods according to the present invention which relate to the in vivo treatment of HIV infections, the present compounds are administered to a patient suffering from HIV in an amount and for a period of time which is sufficient to exert an inhibitory effect on HIV growth, elaboration and replication with one ultimate therapeutic goal being the treatment and/or prevention of AIDS. The present invention also relates to prophylactic treatments to prevent HIV infections in humans.

The present invention also relates to a method for preventing HIV infections which occur during sexual intercourse, the method comprising employing anti-HIV effective doses of acetaminophen or derivates thereof as active ingredients in topical formulations, including suppositories, lubricants, gels, films, or foams for use during intercourse. The method comprises administering a topical formulation comprising an anti-HIV effective amount of one or more pharmaceutically active agents according to the present invention into the vagina or rectum of a subject preferably before sexual intercourse (advisably, in combination with condom protection) in an amount and for a period of time sufficient to exert a protective effect against the sexual transmission of HIV.

Acetaminophen derivatives which may be used in the methods according to the present invention may be represented by the general formula:

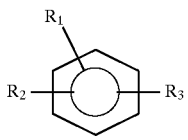

where any one or more of $R^1$, $R^2$ and $R^3$ are substituted in the ortho- (o-), meta (m-) and/or +para (p-) positions of the aromatic (phenyl) core and where $R^1$ is a straight or branched chain $C_1$–$C_8$ alkyl, H, a halogen such as F, Cl, Br and I, trihalomethyl, such as trifluoromethyl and trichloromethyl, hydroxy, alkoxy, such as methoxy (O—$CH_3$), carboalkoxy (—$CO_2R$) such as carbomethoxy, carboxamido (—$CONH_2$), ester, aldehyde, ketone, amino (—$NH_2$), nitro (—$NO_2$), or cyano (—CN) group, or a 5- or 6-membered, saturated or unsaturated heterocyclic ring; $R^2$ may be any substituent defined as being a suitable substituent for $R^1$, a sulfate, phosphate or glucuronide, or a substituted sulfate, phosphate or glucuronide, such that $R^1$ may be bound to $R_2$; and $R^3$ is any substituent defined as suitable for $R^1$ and $R^2$ and can be present with $R^1$ or $R^2$ or both $R^1$ and $R^2$.

DETAILED DESCRIPTION OF THE INVENTION

Figure 1:
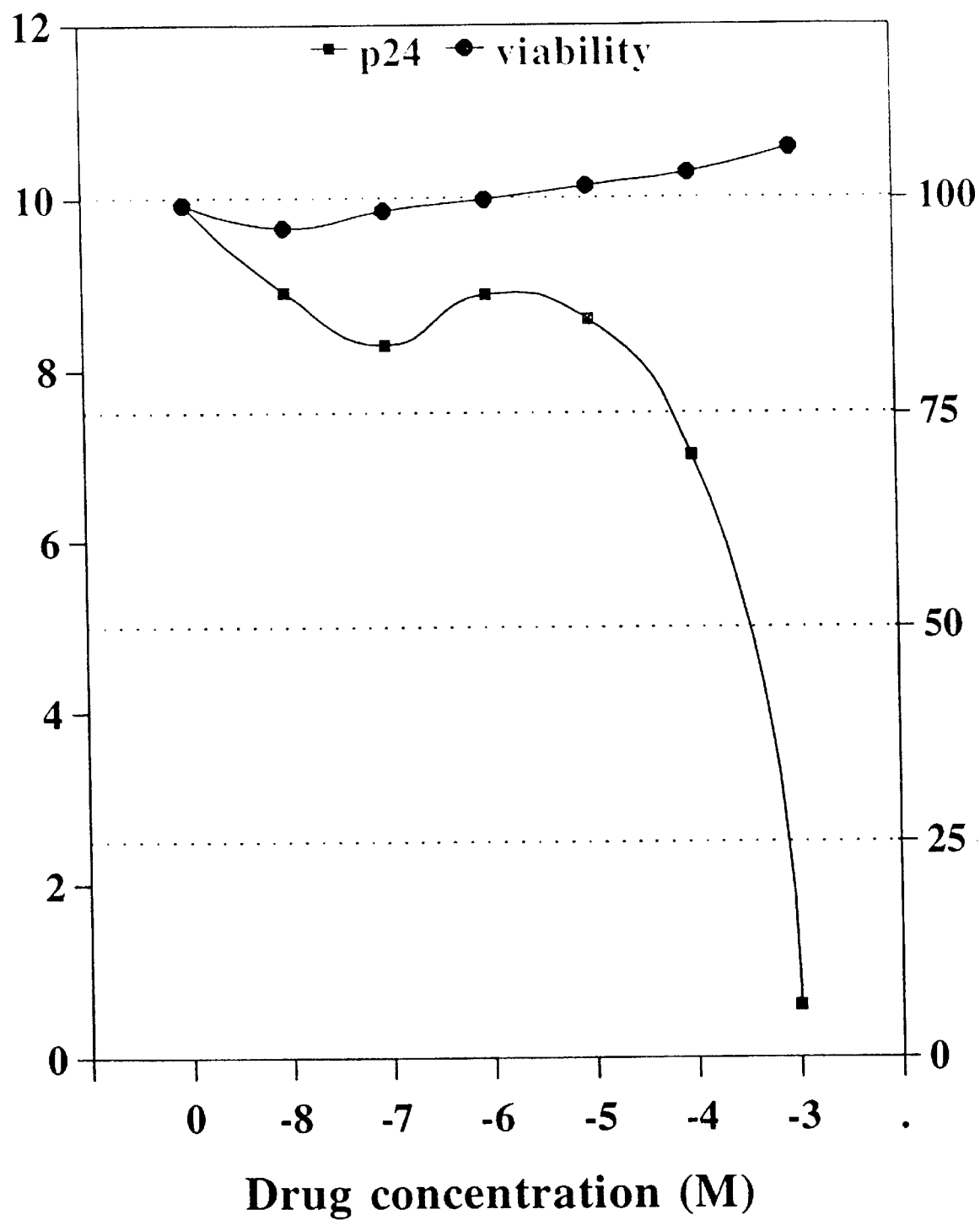
FIG. 1 shows the effect of acetaminophen on reduction of productive HIV infection, as measured by p24 ELISA of MT-4 culture supernatant on day 2, is shown on the left vertical axis as nanograms of p24 per ml (ng/ml). The % values on the right axis were positioned in a fashion that allows estimation of inhibitory effect of the test drug as a function of acetaminophen concentration plotted on the horizontal axis. Complete inhibition of HIV replication was observed at a concentration of acetaminophen equivalent to 150 μg/ml or 1 mM. The experiments were repeated six times and the results of a typical experiment representing the mean of data points from three pooled wells are shown. Effect of XTT assay is shown as percent of control on the right ordinate. Note the absence of correlation between the effect of acetaminophen on cell viability and HIV replication. According to OD values of formazan dye there is no observable toxic dose-effect of acetaminophen even at the highest tested dose containing 0.5% of ethanol. The viability of MT-4 lymphocytes as tested by trypan blue exclusion was similar to control untreated cells. No toxicity was observed when control cells were grown in 0.5% ethanol.

The term "patient" or "subject" is used throughout the specification to describe a human to whom treatment with the compositions and methods according to the present invention is provided.

The term "HIV" is used through the specification to describe Human Immunodeficiency Virus of types 1 and 2 as well as Human T lymphotropic viruses (HTLV) of type 1 and 2 which are human retroviruses and cause adult T cell leukemia and neurodegenerative diseases as well as several other pathogenic retroviruses which can be harmful to humans.

The term "effective concentration" or "effective amount" is used to describe an amount or concentration of an active agent or composition according to the present invention which is used in the present invention to produce an intended result. In the case of the present invention, effective concentrations are generally anti-HIV effective concentrations, which may include concentrations of the active agent which prevent the sexually transmitted spread of HIV. Anti-HIV effective concentrations or amounts are concentrations or amounts of the present compounds which inhibit the replication, growth and elaboration of HIV. In the case of methods for treating HIV infections in patients, the term anti-HIV effective concentration is generally synonymous with the term "therapeutically effective", where the goal of therapy is to inhibit the replication, growth and/or elaboration of HIV in vivo. The term effective concentration or amount subsumes the administration of a pharmaceutically active agent according to the present invention for a period consistent with the realization of the intended result. Effective amounts of the compounds which are used to treat HIV infections in humans include amounts which produce a concentration range in human body fluids of approximately 0.01 µg up to 150 µg per ml, such human body fluids including blood, plasma, serum and lymph fluid.

The present invention relates to the unexpected discovery that acetaminophen and its derivatives exhibit unexpected activity against HIV. In particular, the compounds according to the present invention show potent inhibition of the replication of the virus in combination with low toxicity to the host cells.

The present invention relates to the surprising discovery that acetaminophen and derivatives thereof exhibit unexpected activity against Human Immnodeficiency Virus (HIV). In particular, the compounds according to the present invention show potent inhibition of the replication of the virus in combination with very low toxicity to the host cells (i.e., animal or human tissue). This is an unexpected result.

The present invention also relates to methods for inhibiting the growth or replication of HIV in vitro comprising exposing the virus to an inhibitory effective amount or concentration of acetaminophen or one of its derivatives. This method may be used in comparison tests such as assays for determining the activities of related anti-HIV compounds as well for determining the susceptibility of a patient's strain of HIV infection to one of the compounds according to the present invention.

The therapeutic aspect according to the present invention relates to methods for treating retroviral infections in animal or human patients, and in particular, HIV infections in humans comprising administering anti-HIV effective amounts of the compounds according to the present invention to inhibit the replication, growth and/or elaboration of the viruses in the animal or human patient being treated.

Pharmaceutical compositions based upon the present compounds comprise the active compounds described herein in an inhibitory (i.e., therapeutically) effective amount for treating an HIV infection, optionally in combination with a pharmaceutically acceptable additive, carrier or excipient.

Certain of the compounds, in pharmaceutical dosage form, may be used as prophylactic agents for inhibiting the growth or replication of the viral infection. These may be particularly appropriate as anti-HIV agents. Those agents which exhibit an anti-fertility (contraceptive) effect in addition to an anti-HIV effect may be particularly preferred for use in this aspect of the present invention. In certain pharmaceutical dosage forms, the pro-drug form of the compounds according to the present invention are preferred.

The compounds according to the present invention are produced by synthetic methods which are readily known to those of ordinary skill in the art and include various chemical synthetic methods well known in the art.

During chemical synthesis of the various compounds according to the present invention, one of ordinary skill in the art will be able to practice the present invention without undue experimentation. In particular, one of ordinary skill in the art will recognize the various steps that should be performed to introduce a particular substituent at the desired position of the phenyl group.

The compounds used in the present invention are readily available in the art, or may be synthesized using well-known methods well within the skill set of the routineer. For example, in the case of acetaminophen, this compound may be synthesized by reducing p-nitrophenol with tin in glacial acetic acid with or without acetic anhydride. This compound may also be derived from p-hydroxyacetophenone hydrazone. Methods to synthesize acetaminophen may be found in U.S. Pat. No. 2,998,450 and German patent 453,577. An extensive description of the synthesis of acetaminophen and its derivatives is provided by J. E. Fairbrother in *Analytical Profiles of Drug Substances*, vol. 3, 1974, edited by K. Florey, Academic Press, New York, N.Y., p. 1–109. Metabolic reduction of oral acetaminophen or acetaminophen prodrug forms given intravenously may result in formation of active metabolites, such as sulfates, phosphates or glucuronides and other metabolites, such as acetimidoquinone.

Substituted acetaminophen compounds such as 4'-acetamidophenyl 4-guanidinobenzoate (AGB) are known in the art, for example, as described in U.S. Pat. No. 4,423,069, which is incorporated by reference herein. The '069 patent discloses the synthesis of AGB and other related derivatives. In the '069 patent, AGB is prepared in a coupling procedure in which acetaminophen is reacted with 4-guanidinobenzoic acid hydrohalide in the presence of dicyclohexylcarbodiimide and 4-toluene sulfonic acid as catalyst in a dry solvent such as pyridine or dimethylformamide. The final product is recrystallized from hot ethanol. Related derivatives are synthesized in analogous procedures. One of ordinary skill can readily adapt the procedures which are known in the art to synthesize the compounds used in the present invention.

Pharmaceutical compositions based upon the disclosed acetaminophen chemical compounds or derivatives, thereof comprise the above-described compounds in an inhibitory or therapeutically effective amount for inhibiting the growth, elaboration or replication of HIV or otherwise treating an HIV infection optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route. Intravenous and intramuscular formulations are preferably administered in sterile saline. In the case of compositions which are to be used to inhibit the spread of HIV during intercourse, these compositions generally take the form of gels, ointments, salves or suppositories. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug or metabolite form of the compounds, especially including acylated (acetylated or other) derivatives and other forms of the present compounds such as the phosphate, sulfate or glucuronide may be useful. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within the compositions according to the present invention is an effective amount, whether the desired result is to prevent the spread of HIV by intercourse, for treating the infection or condition in vivo, to suppress HIV infection in vitro or to prevent the transmission of HIV in vitro.

In a preferred embodiment, the present method relates to a treatment for inhibiting the growth, replication or elaboration of HIV in a HIV-infected patient, comprising administering a therapeutically effective amount of one or more of the disclosed acetaminophen or derivatives thereof.

In general, a therapeutically effective amount of the present compound in dosage form usually ranges from slightly less than about 50 mg per day to more than 4 grams per day (or about 1 mg/kg per day to about 60 more mg/kg per day) of the patient or considerably more, depending upon the compound used, the condition or infection treated and the route of administration. In the case of preventing HIV infections by sexual intercourse, the compound is preferably administered into the vagina or rectum in anti-HIV effective amounts, these amounts generally ranging from about 0.5 mg to about 4 grams or more per application.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare the pharmaceutical compositions according to the present invention, an effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed. In the case of formulations to be delivered in effective amounts to vaginal or rectal cavities, such as suppositories, lubricants, foams, gels, films and the like, these may be formulated using standard methods and ingredients/components readily available in the art.

In particularly preferred embodiments according to the present invention, the compounds and compositions are used to treat HIV infections in humans. Generally, to treat HIV infections, the compositions preferably will be administered in oral dosage form in amounts ranging from about 50 micrograms up to about 650 mg. or more from one to eight (preferably one to four) times a day. In therapeutic aspects according to the present invention, the present compounds are preferably administered orally, but may be administered parenterally, topically or in suppository form. Embodiments which are used to prevent HIV infections during sexual intercourse are preferably administered in gel, salve, foam, ointment or suppository form.

The present invention, because of the low toxicity exhibited to the host cells by the disclosed active compounds, may advantageously be employed prophylactically to prevent infection or to prevent the occurrence of clinical symptoms associated with the viral infection. Thus, the present invention also encompasses methods for the prevention or prophylactic treatment of HIV infections. This prophylactic method comprises administering to a patient in need of such treatment an amount of a compound according to the present invention effective for alleviating, and/or preventing the viral infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In this regard, acetaminophen, because of its known low toxicity, is a preferred compound for use in the present invention. In the case of acetaminophen, this compound is administered to the patient in an effective amount, i.e., in an amount ranging from about 250 mg. to about 4 grams per day. This amount is given as a prophylactic agent to an individual who desires to prevent the spread of HIV or alternatively, to prolong the onset of AIDS in a patient.

In addition, compounds according to the present invention may be administered alone or in combination with other agents, especially including other compounds of the present invention. Certain compounds according to the present invention may be effective for enhancing the biological activity of certain agents according to the present invention by reducing the metabolism or inactivation of other compounds and as such, are co-administered for this intended effect. In the case of the present compounds, these compounds may be effectively combined with any one or more of the standard anti-HIV agents which are presently utilized including 3'-azidothymidine (AZT), dideoxycytidine (ddC), and dideoxyinosine (ddI), among others. Additional agents which have shown anti-HIV effects including for example warfarin (oral HIV protease inhibitor), coumarins, bestatin, human chorionic gonadotropin, levamisole, estrogen, progesterone, dexamethasone, indomethacin, cimetidine, and gramicidin which can be combined in effective amounts with compounds according to the present invention to inhibit HIV.

Pursuant to the present invention, experiments evidence that acetaminophen can achieve 50% inhibition of de novo HIV infection at an inhibitory concentration ($IC_{50}$) equal to 21 micrograms per ml ($\mu$g/ml). It has been determined that this concentration and concentrations up to 75-fold higher are not toxic to cells employed in this assay. It is to be noted that the antivirally active concentration of acetaminophen in serum (8–21 $\mu$g/ml) may be readily attained after oral administration of a standard 650 mg dose of said drug every six hours (Steffe et al., J Acquir. Immun. Def Syndr., 3:691–694, 1990). It is thus readily apparent from the favorable therapeutic index demonstrated in these experiments, that oral administration of this or higher doses of acetaminophen can achieve desirable anti-HIV effect in vivo without toxicity to the human host.

Experimental studies have shown that the in vitro activity of effective doses of acetaminophen derivatives are closely associated with the action of equivalent levels of the drug established in vivo. The acetaminophen derivative, 4'-acetamidophenyl 4-guanidinobenzoate (AGB) and substituted phenolic compounds, such as 4'-carboethoxyphenyl 4-guanidinobenzoate (EGB) were reported by Kaminski et al., (Contraception 32:183–189, 1985) to be up to 100-fold more potent than nonoxynol-9 as experimental vaginal contraceptives, but far less toxic and irritating. The contraceptive effect was correlated with inhibitory action on acrosin activity—an enzyme that catalyses the fertilizing capacity of sperm (Bourinbaiar & Lee Huang, Contraception, 51:319–322, 1955).

The present invention relates to the discovery that the acetaminophen derivative, AGB, can display anti-HIV activity in vitro at an $IC_{50}$ equal to 14 $\mu$g/ml and posits that this compound is useful to prevent sex-borne HIV transmission. Therefore, the present invention in a preferred embodiment relates to a method to prevent the transmission of HIV and prevent pregnancy at the same time.

Thus, from the following examples, it can be readily seen that acetaminophen and related acetaminophen derivatives and their pharmaceutically acceptable salts thereof are responsible for the inhibition of the growth, replication and elaboration (spread) of HIV. Further evidence indicates that antiviral doses of these compounds are not correlated with toxicity and that doses defined in vitro will be adequate to prevent and treat HIV.

Having generally described the invention, reference is now made to the following examples intended to illustrate preferred embodiments and comparisons but which are not to be construed as limiting to the scope of this invention as more broadly set forth above and in the appended claims.

EXAMPLE 1

Effect of acetaminophen on HIV infection and T lymphocyte viability

Indicator MT-4 T lymphocytes ($10^5$ cells/ml) were plated in triplicates in 96-well culture plates in the presence of serial 10-fold molar dilutions of test compound. Each culture well contained 180 $\mu$l of RPMI 1640 culture medium with 10% FBS, L-glutamine, penicillin and streptomycin. Immediately thereafter MT-4 lymphocytes were exposed to 20 $\mu$l of viral inoculum corresponding to 100 infectious units per lymphocyte as determined by limiting dilution assay. Two days later—the minimal time period corresponding to full replication cycle of HIV—the culture supernatants were collected and dose-response to drugs was quantitated by measuring the levels of cell-free p24 antigen. The amount of released virus was calculated by comparing the optical density of experimental values from treated wells to commercial p24 standards (Coulter, Hialeah, Fla.).

The toxicity of compounds was tested as follows. MT-4 lymphocytes were grown in the presence or absence of $\log_{10}$ dilutions of test compounds for two days. The cells were then exposed for 4 hours to the preparation of XTT tetrasolium salt (Sigma, St Louis, Mo.) containing phenazine methosulfate (Aldrich, Milwaukee, Wis.). The viability of drug-exposed cells was determined based on activity of mitochondrial hydrogenases of MT-4 converting XTT into color-dense formazan. Optical density was then determined in a plate reader at 450 nM with reference filter at 620 nM and compared to absorbance values of the control cells cultured without drugs. XTT test was also confirmed by trypan blue exclusion test based on the principle that nuclei of dead cells are stained blue.

EXAMPLE 2

Figure 2:
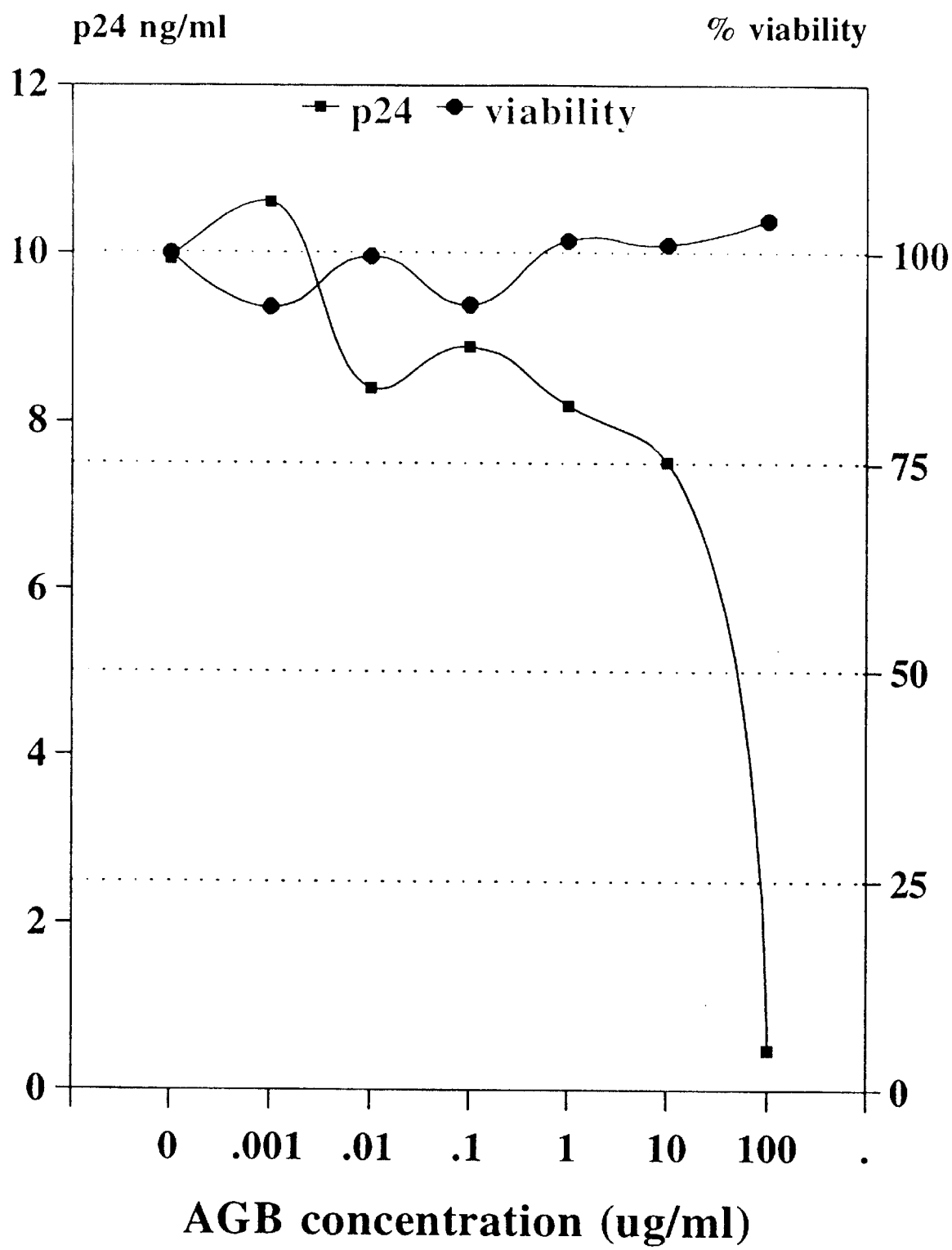
FIG. 2 shows the effect of AGB in preventing HIV transmission as measured by p24 ELISA of MT-4 culture supernatant on day 2 is shown on the left vertical axis as nanograms of p24 per ml (ng/ml). The experiments were repeated at least three times and results of a typical experiment representing the mean of data points from three pooled wells are shown. The % values on the right axis were positioned in a fashion that allows estimation of inhibitory effect of the test drug as a function of AGB concentration plotted on the horizontal axis. Complete inhibition of HIV replication was observed at a concentration of AGB equivalent to 100 µg/ml. Effect of AGB on MT-4 viability following 2 days of continuous exposure as measured by XTT assay is shown as percent of control on the right ordinate. AGB had an effect on HIV replication without affecting the cell viability. According to cytotoxicity test AGB is not toxic to host lymphocytes at 100 µg dose containing 0.5% of ethanol. The viability of MT-4 lymphocytes as tested by trypan blue exclusion was similar to control untreated cells. No toxicity was observed when control cells were grown in 0.5% ethanol.

Effect of 4'-acetamidophenyl 4-guanidinobenzoate (AGB) on HIV infection and T lymphocyte viability The assay conditions are similar to those described in Example 1. The serial ten-fold dilutions of AGB, virus, and cells were left without washing in the culture until tested for HIV production 2 days later. Topical contraceptive agents nonoxynol-9 and gramicidin were used as controls. The effect of AGB on release of gag p24 protein of HIV and viability is shown in FIG. 2. The results reveal that complete inhibition of HIV was achieved in the presence of 100 µg/ml of AGB—a nontoxic dose corresponding to the previously reported optimal concentration required to inhibit both acrosome reaction and sperm motility in vitro with human spermatozoa and in animal studies. The toxicity tests have not demonstrated any reduction in viability of MT-4 at this concentration.

EXAMPLE 3

Figure 3:
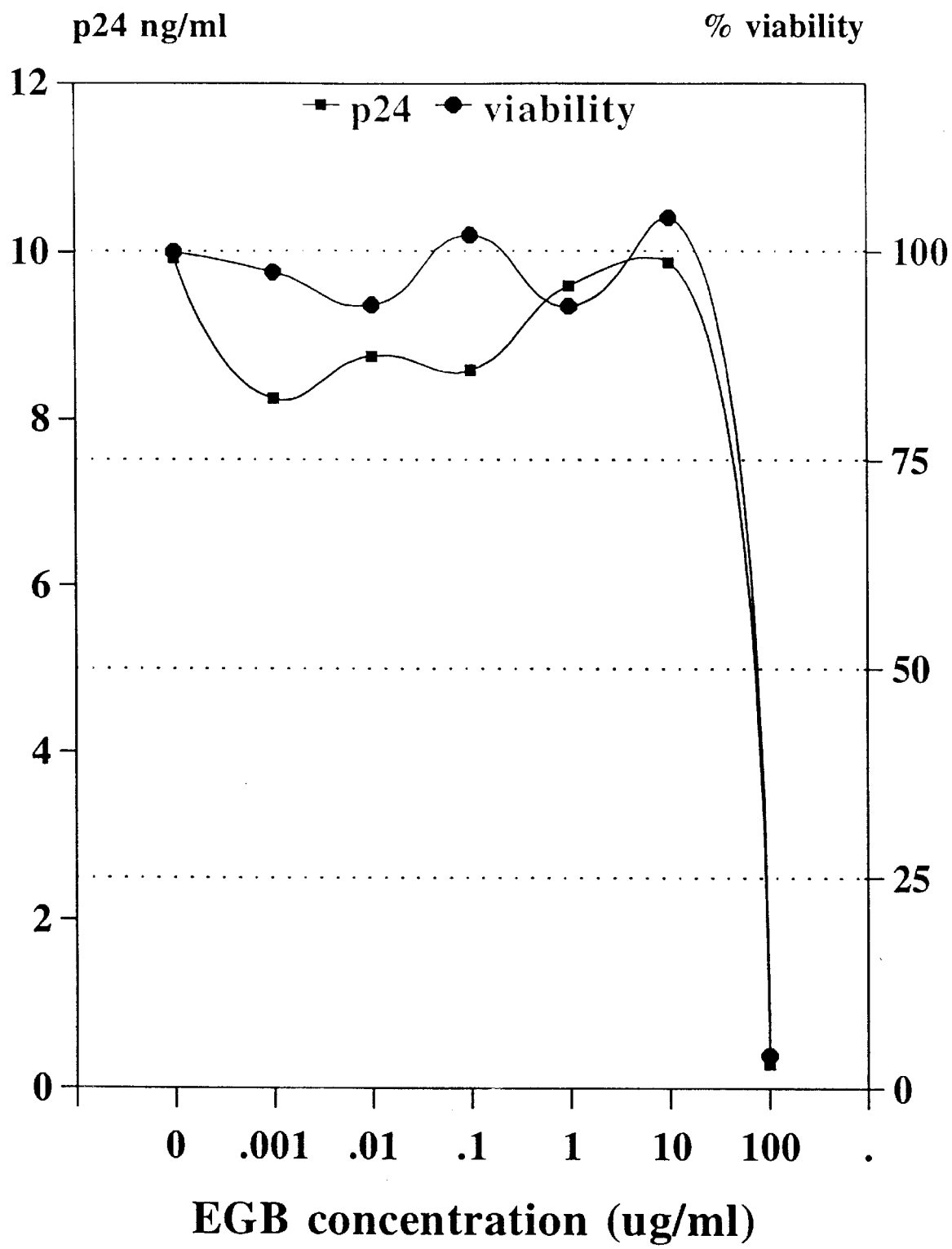
FIG. 3 shows the effect of EGB in preventing HIV transmission as measured by p24 ELISA shown as nanograms of p24 per ml (ng/ml) on the left axis. The experiments were repeated at least three times and results of a typical experiment representing the mean of data points from three pooled wells are shown. The % values on the right axis were positioned in a fashion that allows estimation of the inhibitory effect of test drug as a function of EGB concentration plotted on the horizontal axis. The inhibition of HIV replication was observed only at concentration of EGB equivalent to 100 µg/ml. However, this dose was also toxic to host cells as shown by toxicity assay, indicating that antiviral activity was not specific and due to the death of host lymphocytes. The death of MT-4 lymphocytes, which occurred in the presence of EGB equivalent to 100 µg/ml, was also confirmed by trypan blue exclusive test. No toxicity was observed when control cells were grown in 0.5% ethanol.

Effect of 4'-carboethoxyphenyl 4-guanidinobenzoate (EGB) on HIV infection and T lymphocyte viability The assay conditions are similar to those described in Example 1. The serial ten-fold dilutions of EGB, virus, and cells were left without washing in the culture until tested for HIV production 2 days later. Topical contraceptive agents nonoxynol-9 and gramicidin were used as controls. The effect of EGB on release of gag p24 protein of HIV and viability is shown in FIG. 3. The results reveal that complete inhibition of HIV was achieved in the presence of 100 µg/ml of AGB. However, this dose was toxic to host cells. EGB had no effect on HIV infection at doses that were not toxic. The results indicate that the acetaminophen core or nucleus determines the anti-HIV activity.

The results summarized in Table 1 compare relative activities of acetaminophen, AGB and EGB on HIV infectivity and cell viability. For the sake of comparison the effects of unrelated, topical contraceptive agents with anti-HIV activity, nonoxynol-9 and gramicidin, are also shown. EGB, has not shown specific anti-HIV activity. AGB, though 10 times less potent as an antiviral compound than nonoxynol-9, shows no concurring cytotoxicity at the effective dose—indicating that AGB has a better selectivity index. Although gramicidin, another contraceptive and antiviral agent discovered by the inventor, has even better selectivity this compound is toxic at doses that are a thousand-fold lower than AGB. Acetaminophen, though antivirally active, has not shown any toxicity at all tested concentrations.

TABLE 1

Approximate orders of anti-HIV concentrations (IC) of topical contraceptives in relation to cytotoxicity (CC)

| Compounds | $IC_{100}$ | $CC_{100}$ | $SI^a$ |
|---|---|---|---|
| Acetaminophen | 150 µg | $ND^b$ | ND |
| AGB | 100 µg | 10 mg$^c$ | 100 |
| EGB | 100 µg | 100 µg | 1 |
| Nonoxynol-9 | 10 µg | 10 µg | 1 |
| Gramicidin | 10 ng | 10 µg | 1,000 |

[a]SI is the selectivity index and was determined as the ratio between $CC_{100}$ and $IC_{100}$ values.
[b]Not determined since no cytotoxicity was observed at the highest tested 1 mM dose.
[c]MT-4 cells suspended in stock 50% ethanol solution of AGB. The viability of cells grown for 2 days in 1 mg/ml of AGB was approximately 30% of the control. No cytotoxicity was observed at 100 µg/ml-the highest tested dose in anti-HIV assays.

Conclusions

In conclusion, it has been established by this inventor that acetaminophen or pharmaceutically acceptable substituted salts are responsible for anti-HIV activity. The results presented in the 3 drawings and in table 1 demonstrate that acetaminophen and derivatives thereof are effective against HIV infection in vitro at doses that are not toxic. The doses that were effective can be attained in vivo either by oral administration of acetaminophen and derivatives thereof or by topical application of topical formulations containing as an active ingredient said drugs. The formulation containing acetaminophen and derivatives thereof as active ingredients may be suitably administered together with a pharmaceutically acceptable carrier known in the art. The exact form of delivery will depend on particular need, being either systemic treatment of HIV infection or prevention of transmission and spread of HIV upon sexual intercourse.

The appropriate dosages for an individual subject will depend on the levels of acetaminophen or pharmaceutically acceptable derivatives thereof attained in blood, serum, plasma, and other human body fluids such as semen and vaginal or rectal excretions. The levels not higher than 1 mM or 150 µg/ml for systemic use and topical doses not higher than 1 M or 150 mg/ml are preferable. The doses for systemic use can be given once a day or divided doses may be administered daily for a period of time as indicated by the exigencies of the therapeutic situation. The doses for topical use can be administered preferably before sexual intercourse. The maximum daily dose for either use should not be higher than 7,500 mg. The use of higher doses would be limited by physical capacity of the human body to accommodate said doses or by overdose-associated toxicity. Although the toxicity can be reversed by giving glutathione restoring agents which may also have anti-HIV activity, e.g., N-acetylcysteine, the preferred dosage must be within acceptable non-toxic range given for a period of time deemed necessary. Acetaminophen or pharmaceutically acceptable substituted salts can be used with or without N-acetylcysteine or related compounds of similar activity on glutathione metabolism. Effective amount of acetaminophen or pharmaceutically acceptable substituted salts thereof as agents possessing anti-HIV activity can be also given in combination with other compounds selected from a group specified in the body of invention including but not limited to warfarin (oral HIV protease inhibitor), coumarins, bestatin, human chorionic gonadotropin, levamisole, estrogen, progesterone, dexamethasone, indomethacin, cimetidine, and gramicidin. The lowest possible effective dosage can be calculated so as to attain sufficient levels of acetaminophen or pharmaceutically acceptable derivatives thereof to achieve optimal activity in combination or alone. The concentration ranges set forth herein are exemplary only and not intended to limit the scope or practice of invention. The adjustment and optimization of dosage is obvious to those of skill in the art and it is apparent that certain changes and modifications may be practiced within the scope of the appended claims.

It is to be understood by those skilled in the art that the foregoing description and examples are illustrative of practicing the present invention, but are in no way limiting. Variations of the detail presented herein may be made without departing from the spirit and scope of the present invention as defined by the following claims.

I claim:

1. A method for treating an HIV infection in a human comprising administering to said human an anti-HIV effective amount of a compound having the formula:

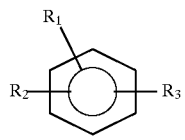

where any one or more of $R^1$, $R^2$ and $R^3$ are substituted in the ortho- (o-), meta (m-) and/or para (p-) positions of the aromatic (phenyl) core and where $R^1$ is a straight or branched chain $C_1$–$C_8$ alkyl, H, F, Cl, Br, I, trihalomethyl, hydroxy, alkoxy, carboalkoxy, carboxamido, ester, aldehyde, ketone, amino, nitro or cyano;

$R^2$ may be the same substituent as $R^1$, a sulfate, phosphate or glucuronide, or a substituted sulfate, phosphate or glucuronide; and $R^3$ may be the same substituent as $R^1$ or $R^2$ and can be present with $R^1$ or $R^2$ or both $R^1$ and $R^2$, with the proviso that $R^1$, $R^2$ and $R^3$ are not all H, said compound being administered for a period of time sufficient to exert an inhibitory effect on said HIV infection.

2. The method according to claim 1 wherein said carboalkoxy is carbomethoxy.

3. The method according to claim 1 wherein said alkoxy is methoxy.

4. The method according to claim 1 wherein said trihalomethyl is trichloromethyl or trifluoromethyl.

5. A method for inhibiting the growth, replication or elaboration of HIV in humans with an HIV infection comprising administering to said humans an amount of a compound having the formula:

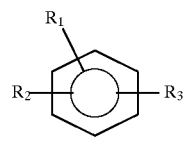

where any one or more of $R^1$, $R^2$ and $R^3$ are substituted in the ortho- (o-), meta (m-) and/or para (p-) positions of the aromatic (phenyl) core and where $R^1$ is a straight or branched chain $C_1$–$C_8$ alkyl, H, F, Cl, Br, I, trihalomethyl, hydroxy, alkoxy, carboalkoxy, carboxamido, ester, aldehyde, ketone, amino, nitro or cyano;

$R^2$ may be the same substituent as $R^1$ a sulfate, phosphate or glucuronide, or a substituted sulfate, phosphate or glucuronide; and $R^3$ may be the same substituent as $R^1$ or $R^2$ and can be present with $R^1$ or $R^2$ or both $R^1$ and $R^2$, with the proviso that $R^1$, $R^2$ and $R^3$ are not all H, effective to produce a concentration range in human body fluids within the range of about 0.01 µg to about 150 µg per ml.

6. The method according to claim 1 wherein said carboalkoxy is carbomethoxy.

7. The method according to claim 1 wherein said alkoxy is methoxy.

8. The method according to claim 1 wherein said trihalomethyl is trichloromethyl or trifluoromethyl.

9. The method according to claim 1 wherein said compound is acetaminophen.

10. The method according to claim 1 wherein said body fluid is selected from the group consisting of blood, plasma, serum semen and lymph fluid.

11. The method according to claim 9 wherein said body fluid is selected from the group consisting of blood, plasma, serum semen and lymph fluid.

12. The method according to claim 1 wherein said compound is administered combination with an effective amount of at least one agent selected from the group consisting of AZT, ddC, ddI, warfarin, coumarins, bestatin, human chorionic gonadotropin, levamisole, estrogen, progesterone, dexamethasone, indomethacin, cimetidine, gramicidin and mixtures thereof.

13. A method of treating an HIV infection in a human comprising administering to said human an anti-HIV effective amount of a compound selected from the group consisting of acetaminophen and 4'-acetamidophenyl 4-guanidinobenzoate for a period of time sufficient to exert an inhibitory effect on said HIV infection.

14. The method according to claim 13 wherein said compound is acetaminophen.

15. The method according to claim 13 wherein said compound is 4'-acetamidophenyl 4-guanidinobenzoate.

* * * * *